(12) United States Patent
Fialkov et al.

(10) Patent No.: US 12,114,847 B2
(45) Date of Patent: Oct. 15, 2024

(54) DEEP ORBITAL ACCESS RETRACTOR

(71) Applicant: SUNNYBROOK RESEARCH INSTITUTE, Toronto (CA)

(72) Inventors: Jeffrey Allan Fialkov, Toronto (CA); Glenn Patrick Edwards, Toronto (CA)

(73) Assignee: SUNNYBROOK RESEARCH INSTITUTE, Toronto (CA)

(*) Notice: Subject to any disclaimer, the term of this patent is extended or adjusted under 35 U.S.C. 154(b) by 414 days.

(21) Appl. No.: 17/429,857

(22) PCT Filed: Feb. 11, 2020

(86) PCT No.: PCT/CA2020/050181
§ 371 (c)(1),
(2) Date: Aug. 10, 2021

(87) PCT Pub. No.: WO2020/163950
PCT Pub. Date: Aug. 20, 2020

(65) Prior Publication Data
US 2022/0133294 A1 May 5, 2022

Related U.S. Application Data

(60) Provisional application No. 62/803,884, filed on Feb. 11, 2019.

(51) Int. Cl.
A61B 17/02 (2006.01)
A61B 17/00 (2006.01)

(52) U.S. Cl.
CPC ...... *A61B 17/0231* (2013.01); *A61B 17/0206* (2013.01); *A61B 2017/00862* (2013.01)

(58) Field of Classification Search
CPC ............ A61B 17/0231; A61B 17/0206; A61B 2017/0212
See application file for complete search history.

(56) References Cited

U.S. PATENT DOCUMENTS 4,321,916 A * 3/1982 McKee ............ A61F 9/007
                                              600/209
5,339,803 A   8/1994 Mayzels et al.
(Continued)

OTHER PUBLICATIONS

International Search Report for PCT/CA2020/050181 dated Jun. 2, 2020.

*Primary Examiner* — Ellen C Hammond
*Assistant Examiner* — Holly Joanna Lane
(74) *Attorney, Agent, or Firm* — HILL & SCHUMACHER

(57) ABSTRACT

The present disclosure provides a deep orbital access retractor (DOAR) device which includes a manipulable body section including a compressible handle having a size and shape to be manipulated by at least two (2) digits of a clinician. A flexible head section having two (2) arms with each arm having a distal end and a proximal end, with the distal ends of the arms spaced apart forming a gap therebetween at a distal tip section. A flexible flange material envelops and encloses the two arms and the gap and extends around a periphery of the flexible head section. A flexible diaphragm is attached to and extends between the two arms to provide a generally spoon-shaped flexible head section. The flexible head section is linked to the compressible handle section with the linkage being configured such that upon compression of the handle section the arms articulate with respect to each other thereby causing narrowing of the flexible head section to allow for insertion into the orbit and positioning between soft tissue and bone while the flexible diaphragm remains in sufficient tension to not obstruct the view of the operator into the orbit. When compression is released the flexible diaphragm develops sufficient tension and rigidity for applying sufficient force to retract the orbital contents of a patient to allow access to orbital walls.

19 Claims, 14 Drawing Sheets

(56) References Cited

U.S. PATENT DOCUMENTS

| | | |
|---|---|---|
| 8,758,235 B2 | 6/2014 | Jaworek et al. |
| 9,717,489 B2 | 8/2017 | Knoepfle et al. |
| 2005/0080425 A1* | 4/2005 | Bhatnagar .............. A61B 17/02 |
| | | 606/90 |
| 2007/0060795 A1* | 3/2007 | Vayser ................. A61B 17/025 |
| | | 600/245 |
| 2007/0225568 A1* | 9/2007 | Colleran ............ A61B 17/0206 |
| | | 600/201 |
| 2009/0149716 A1* | 6/2009 | Diao ................. A61B 17/0218 |
| | | 600/207 |
| 2011/0077468 A1* | 3/2011 | Finger ................ A61B 17/0231 |
| | | 600/236 |
| 2014/0228868 A1* | 8/2014 | Hassan .............. A61B 17/0057 |
| | | 606/153 |

* cited by examiner

DEEP ORBITAL ACCESS RETRACTOR

FIELD

The present disclosure relates to a deep orbital access retractor (DOAR) device designed as a flexible and expandable retractor to be able to conform to the contour of each individual patient's orbital walls to create a sealed barrier to the fat, muscle and other soft tissues that would otherwise pass through any gaps between the retractor and the boney wall thus impeding vision of and access to the surgical field.

BACKGROUND

Surgery of the boney eye-socket (orbit) is performed when injuries, cancers or birth defects change the shape and structure of the orbit, composed of four boney walls that converge at one end. Fractures of the eye socket occur very commonly as a result of trauma. The boney walls of the eye-socket, in these instances, must be reconstructed to ensure restoration of full function and appearance of the eye and its surrounding tissues.

Visualization of these walls in order to improve accuracy of surgery with better control and instrumentation is a technical challenge experienced by all surgeons that perform orbital surgery (plastic surgeons, ophthalmologists, otolaryngologists, etc.) This is because the eye socket is a very tight space filled with soft tissues (fat, muscle, globe, etc.) that move around fluidly when displaced and must be held back under pressure to facilitate visualization of one or more of the walls.

Insertion of orbital implants, used to reconstruct orbital walls removed for cancer, or deficient as a result of trauma or birth abnormalities, require full visualization of the circumferential bone (for instance, the ledges of a hole in the bone) upon which the implant must sit to be stable and to fully restore the normal contour. Inadequate visualization of boney ledges and/or incorrect implant placement upon them can result in prolonged operative times and a number of complications including: restricted eye movement, displacement of the globe, double vision, etc.

Current surgical orbital insert retractable devices and retractors suffer from several drawbacks, including the fact that they are rigid and do not conform to the walls of the orbit to withhold the soft tissues. Inevitable gaps between these metal retractors and the bony walls allow the soft tissue to "spill" into the operative field thereby impeding visualization and instrumentation which adds to operating time and reduces the accuracy of surgery and surgical reconstruction. The latter may result in significant complications such as muscle entrapment (restricted eye movement), globe displacement as a consequence of improper placement of implants or damage to vital structures as a consequence of poor visualization and poor retraction of those structures. Furthermore, the rigidity of current retractors results in significant compression of the orbital contents during retraction which in turn can cause injury.

In addition, pre-existing orbital retractor designs show the expanding head of the retractor made from a material similar to the frame (ie: stainless steel and/or titanium) with significant rigidity throughout the entire assembly. Further, the head is divided into a series of flat or concave plates that fan out from a central hinge located at the tip. They are rigidly fixed at this point and can only rotate about this point. The uniform edges of the plates designed to make contact with the soft tissue and bone are rigid. These edges do not conform to the orbital walls and they do not seal off the orbital contents from the orbital defect.

Therefore it would be very advantageous to provide a deep orbital access retractor (DOAR) device that addresses the above-noted deficiencies and provides a flexible head section that gives a larger number of degrees of freedom of movement of the retractor during manipulation by the Operator.

SUMMARY

The deep orbital access retractor device disclosed herein is designed as a flexible and expandable retractor to be able to conform to the contour of each individual patient's orbital walls, regardless of anatomic variation, to create a sealed barrier to the fat, muscle and other soft tissues that would otherwise pass through any gaps between the retractor and the boney wall, obscuring the surgeons view and impeding instrumentation. The latter is needed to replace or restore the broken, missing or deficient wall or floor or to remove bone for tumour ablation, decompression of the eye socket or access to structures adjacent to the eye-socket. Current retractors are rigid (metal) and are sub-optimal in that they do not adequately conform to the walls of the orbit to act to withhold the soft tissue contents out of view. Gaps between the metal retractors and the boney walls allow the soft tissues to pass through (herniate) into the operative field impeding visualization and or the passage of instruments or implants.

The present disclosure provides a deep orbital access retractor, comprising:
  a) a compressible handle section having a size and shape to be manipulated by at least two (2) digits of a clinician;
  b) a flexible head section having two (2) arms with each arm having a distal end and a proximal end, said distal ends of said arms spaced apart forming a gap therebetween at a distal tip section, a flexible flange material enveloping and enclosing said two arms and said gap and extending around a periphery of said flexible head section, and including a flexible diaphragm attached to and extending between said to arms to provide a generally spoon-shaped flexible head section; and
  c) said flexible head section being linked to said compressible handle section with said linkage between said compressible handle section and said proximal ends of said trailing arms being configured such that upon compression of said handle section said arms articulate with respect to each other thereby causing narrowing of the flexible head section to allow for insertion into the orbit and positioning between soft tissue and bone while said flexible diaphragm remains in sufficient tension to not obstruct the view of the operator into the orbit, and wherein when compression is released the flexible diaphragm develops sufficient tension and rigidity for applying sufficient force to retract the orbital contents of a patient to allow access to orbital walls.

The flange material enveloping and enclosing the two arms and the gap may have a material density variation in a vicinity of the gap configured to produce a hinge-like structure of the distal tip section that provides asymmetrical or universal movement and out-of-plane movement of the distal ends of the arms.

The deep orbital access retractor may include a deformable material located in the gap between the distal ends of the arms and abutting against the distal ends of the arms.

The present disclosure provides a deep orbital access retractor, comprising:

a) a compressible handle section having a size and shape to be manipulated by at least two (2) digits of a clinician;

b) a flexible head section having two geometrically opposed and arc-shaped arms each having a proximal end and a distal end, the distal ends of the arc-shaped arms being spaced from each other by a gap at a distal tip section, each trailing arc-shaped arm being linked at its proximal end to the compressible handle section, a flexible flange material attached to the arc-shaped arms and extending around a periphery of the flexible head section and enclosing the gap at the distal tip section, a flexible diaphragm attached to and extending between the arc-shaped arms, the distal ends of the arc-shaped arms having a geometry and shape and the flange material enveloping the distal tip section having a material density variation configured to produce a hinge-like structure of the distal tip section that provides asymmetrical or universal movement and out-of-plane movement of the distal ends of arc-shaped arms; and the linkage between the compressible handle section and the proximal ends of the arc-shaped arms being configured such that upon compression of the handle section the arms articulate with respect to each other thereby causing narrowing of the flexible head section to allow for insertion into the orbit and positioning between soft tissue and bone while the flexible diaphragm remains in sufficient tension to not obstruct the view of the operator into the orbit, and wherein when compression is released the diaphragm develops sufficient tension and rigidity for applying sufficient force to retract the orbital contents of a patient to allow access to the orbital walls.

The flange material enveloping and enclosing the two arc-shaped arms and the gap may have a material density variation in a vicinity of the gap configured to produce a hinge-like structure of the distal tip section that provides asymmetrical or universal movement and out-of-plane movement of the distal ends of the arc-shaped arms.

The deep orbital access retractor may include a deformable material located in the gap between the distal ends of the arc-shaped arms and abutting against the distal ends of the arc-shaped arms.

The present disclosure provides a deep orbital access retractor, comprising:

a) a manipulable body section including a handle and two geometrically opposed handle arms each having a distal end and a proximal end, the proximal ends being hinged on the handle; and b) a flexible head section having two geometrically opposed and arc-shaped trailing arms each having a proximal end and a distal end with each trailing arm being hinge connected at its proximal end to a corresponding distal end of one of the opposed handle arms, the distal ends of the arc-shaped trailing arms being spaced from each other by a gap at a distal tip section, each of the arc-shaped trailing arms and the gap being enveloped by a flexible flange material extending around a periphery of the flexible head section, a flexible diaphragm being connected to the trailing arms to form a generally spoon shaped flexible head section, the distal ends having a geometry and shape and the flange material enveloping the distal tip section having a material density variation configured to produce a hinge-like structure of the distal tip section that provides asymmetrical or universal movement and out-of-plane movement of the distal ends of trailing arms; and the opposed handle arms coupled to a biasing mechanism configured to bias the opposed handle arms away from each other, and whereupon when a clinician squeezes the opposed handle arms together the distal ends of the opposed handle arms and the proximal ends of the arc-shaped trailing arms come together thereby causing narrowing of the flexible head section to allow for insertion into the orbit and positioning between soft tissue and bone while the flexible diaphragm remains in sufficient tension to not obstruct the view of the operator into the orbit, and wherein when compression is released the diaphragm develops sufficient tension and rigidity for applying sufficient force to the orbital contents of a patient to allow access to the orbital walls.

The biasing mechanism may be a spring mechanism with the opposed arms coupled to the spring mechanism which is configured to bias the opposed arms away from each other, and whereupon when a clinician squeezes the opposed arms together the distal ends of the opposed arms and the proximal ends of the trailing arms come together thereby causing the flexible diaphragm to sufficient tension and rigidity for applying sufficient force to the orbital contents of a patient to allow access to the orbital wall.

The device may include a flexible material separating the distal ends of the opposed arms and the proximal ends of the trailing arms in each hinge connection to provide an extra degree of freedom of movement of the opposed arms and the proximal ends of the trailing arms.

The device may include a flexible material separating the proximal ends of the opposed arms in the hinge connection in the handle to provide an extra degree of freedom of movement of the opposed arms and the proximal ends of the trailing arms.

The device may include a flexible material located in the gap separating the distal ends of the trailing arms to provide an extra degree of freedom of movement of the distal ends of the trailing arms.

The device may further comprise a camera mounted on the handle having a field of view which includes the flexible head section.

The deep orbital access retractor device may include at least one light source mounted thereon to illuminate a surgical area of a patient that the device is being used on.

The deep orbital access retractor device may include a light source mounted on each hinge connection of the trailing arms to the geometrically opposed arms.

Each light source may be a light emitting diode.

The device may include a power supply located in the handle which is electrically connected to the camera and the light source.

This spring mechanism may be built into the geometrically opposed arms.

The deep orbital access retractor device may further comprise finger pads mounted adjacent to the proximal ends of the geometrically opposed arms and having size and shape to accommodate the fingers of a clinician.

The flexible diaphragm and the flexible flange may be a single unitary piece made of the same material with the flexible flange being thicker than the flexible diaphragm so that it is more rigid than the flexible diaphragm.

The flexible diaphragm and the flexible flange may be made of separate materials with the flexible flange section being made of a material that is more rigid than the flexible diaphragm, and the flexible diaphragm may be bonded to the flexible flange.

A further understanding of the functional and advantageous aspects of the present disclosure can be realized by reference to the following detailed description and drawings.

BRIEF DESCRIPTION OF THE DRAWINGS

Embodiments will now be described, by way of example only, with reference to the accompanying drawings, in which:

FIG. 11 shows the retractor with frame in closed, bent (right panel) position and the left panel is similar;

FIG. 12 shows the retractor with frame in closed, straight position;

DETAILED DESCRIPTION

Figure 1:
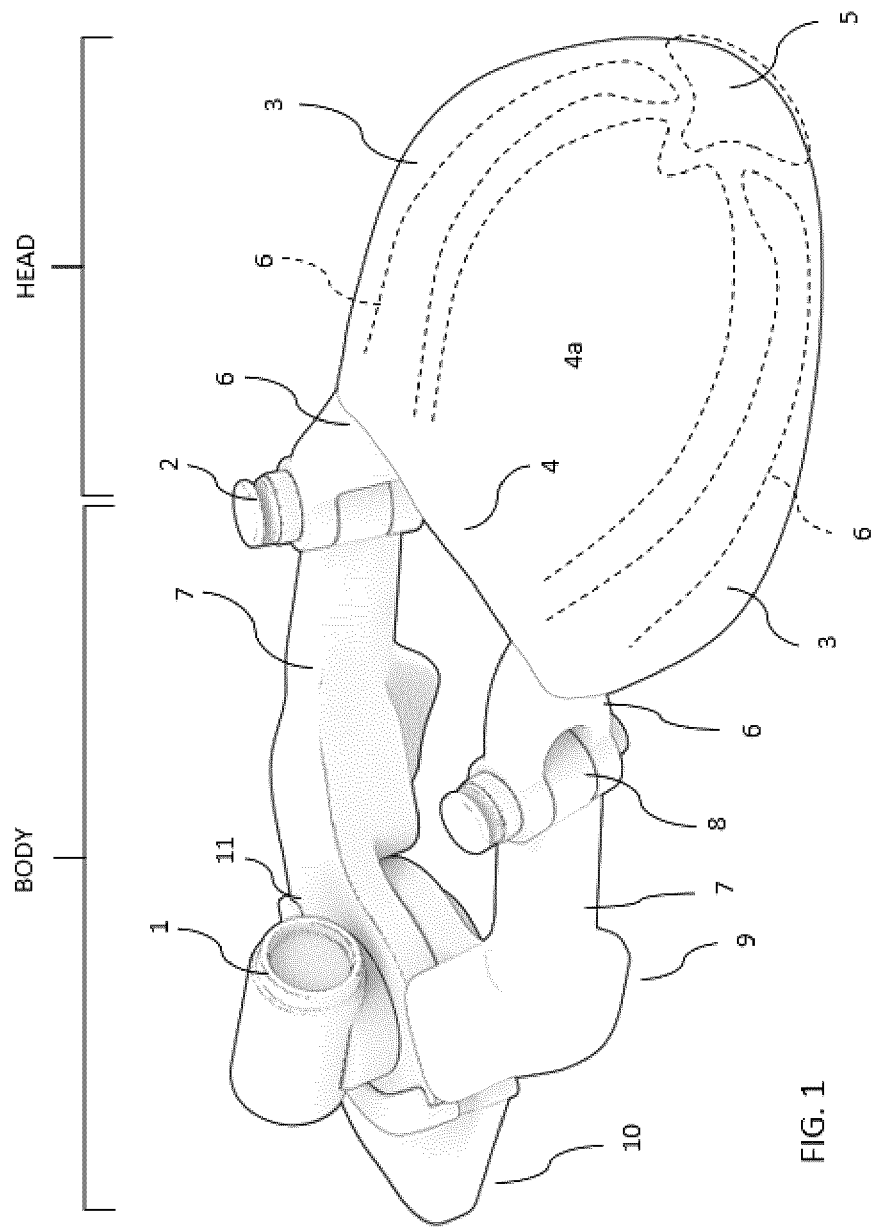
FIG. 1 shows orthographic view of an embodiment of the deep orbital access retractor (DOAR) showing primary components.

Various embodiments and aspects of the deep orbital access retractor device disclosed herein will be described with reference to details discussed below. The following description and drawings are illustrative of the disclosure and are not to be construed as limiting the disclosure. The figures are not to scale. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one nonlimiting example, the terms "about" and "approximately" mean plus or minus 10 percent or less.

As used herein, the terms "generally" and "essentially" are meant to refer to the general overall physical and geometric appearance of a feature and should not be construed as preferred or advantageous over other configurations disclosed herein.

PARTS LIST

1—Camera/Sensor Assembly
2—LED Light
3—Flexible Flange
4a—Elastic Diaphragm (or Elastic Sling)
4—Proximal Edge of elastic diaphragm 4a
5—Flexible Tip with Integrated Hinge
6—Trailing Arm
7—Power Arm
8—Hinge
9—Finger Pad
10—Handle
11—Guide/Mount/Barrier
12—Integrated Spring Mechanism
13—Hole/Mount The present deep orbital access retractor includes a compressible body/handle section having a size and shape configured to be manipulated by a clinician, preferably using two (2) digits. The retractor includes flexible head section which has a generally spoon shape. The spoon shape of the flexible head is achieved by having two geometrically opposed and arc-shaped trailing arms each having a proximal and distal end, with the distal ends being spaced from each other by a gap at a distal tip section, while the proximal ends are linked to the compressible handle section. A flexible flange material envelops the trailing arms as well as the gap between distal ends of the arms and extends around the periphery of the flexible head section. A flexible diaphragm is attached to, and extends between the trailing arms thereby giving the flexible head section its spoon shape.

The compressible handle section is linked to this flexible head section with the linkage configured so when the handle is compressed, the diameter of the flexible head section decreases and diaphragm maintains tension and rigidity in spite of that compression, and when the handle is released by the clinician so that it is no longer compressed, the tension increases because the arms move apart from each other.

As a non-limiting embodiment, the handle or body section may simply be two separate rigid members with one attached to the proximal end of one of the trailing arms and the other rigid member being attached to the proximal end of the other trailing arm. These rigid members are shaped and dimensioned so that the clinician can grasp them with two digits and upon squeezing or compressing them together the trailing arms articulate with respect to each other (the proximal ends move close to each other) thereby causing narrowing of the flexible head section to allow for insertion into the orbit and positioning between soft tissue and bone while the flexible diaphragm remains in sufficient tension so as to not obstruct the view of the operator into the orbit.

In the compressed state, the clinician inserts the flexible head section into the patient between the eye ball and orbit, and upon the clinician releasing compression such that the proximal ends of the trailing spread apart to the open position, the head section expands back towards its original diameter thus abutting the orbital sidewalls and sealing the space and the diaphragm develops sufficient tension and rigidity for applying sufficient force to retract the orbital contents of a patient to allow access to the orbital walls for the surgical procedure to carry out repairs. Once the repairs are made, the insertion process is reversed to remove the retractor.

A more extensive handle/body section may be included, for example, instead of the above-mentioned two separate rigid members each attached to an associated trailing arm, in another non-limiting embodiment the handle may be a continuous compressible loop having two adjacent ends with one end attached to the proximal end of one trailing arm and the other adjacent end attached to the proximal end of the other trailing arm. In this case the loop has a sufficient diameter so that upon the clinician compressing the two spaced sides of the loop, the proximal ends of the trailing arms come together to cause the diameter of the flexible head section to decrease as discussed above.

Figure 3:
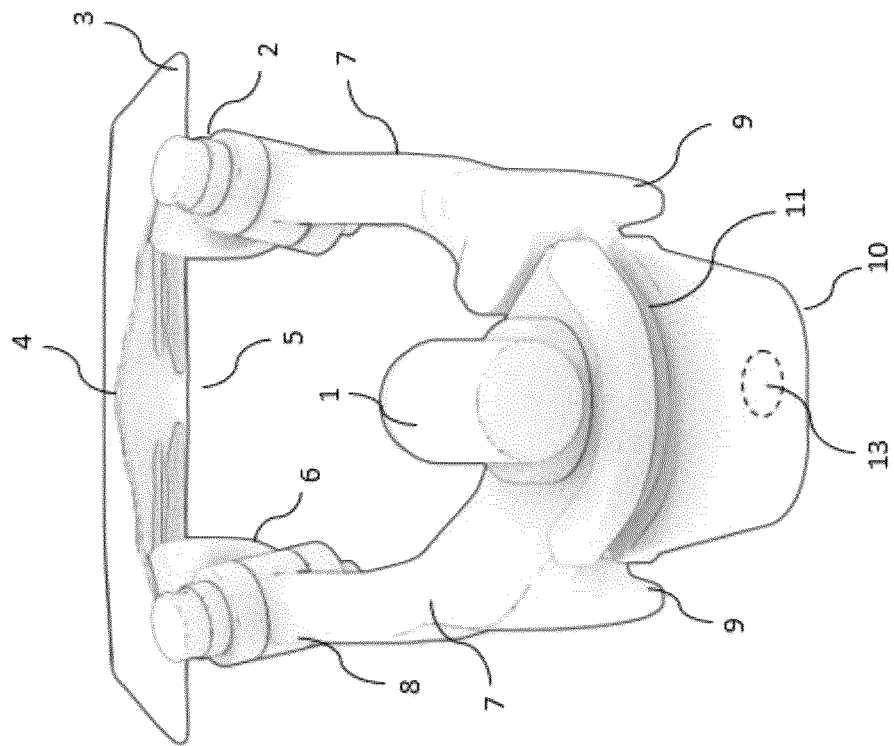
FIG. 3 is a back view of the device of FIG. 1.
Figure 2:
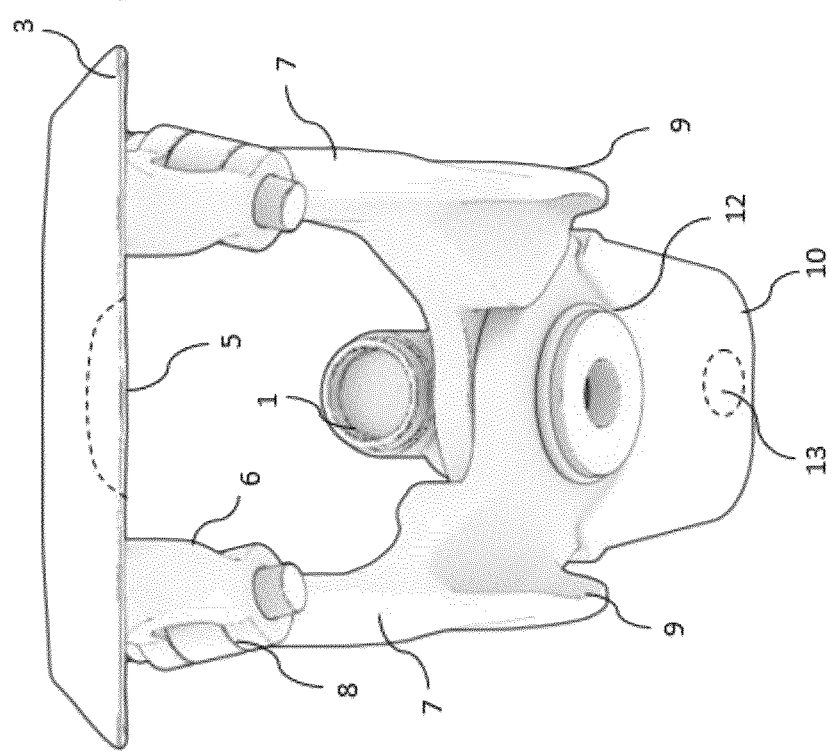
FIG. 2 is a front view of the device of FIG. 1.
Figure 4:
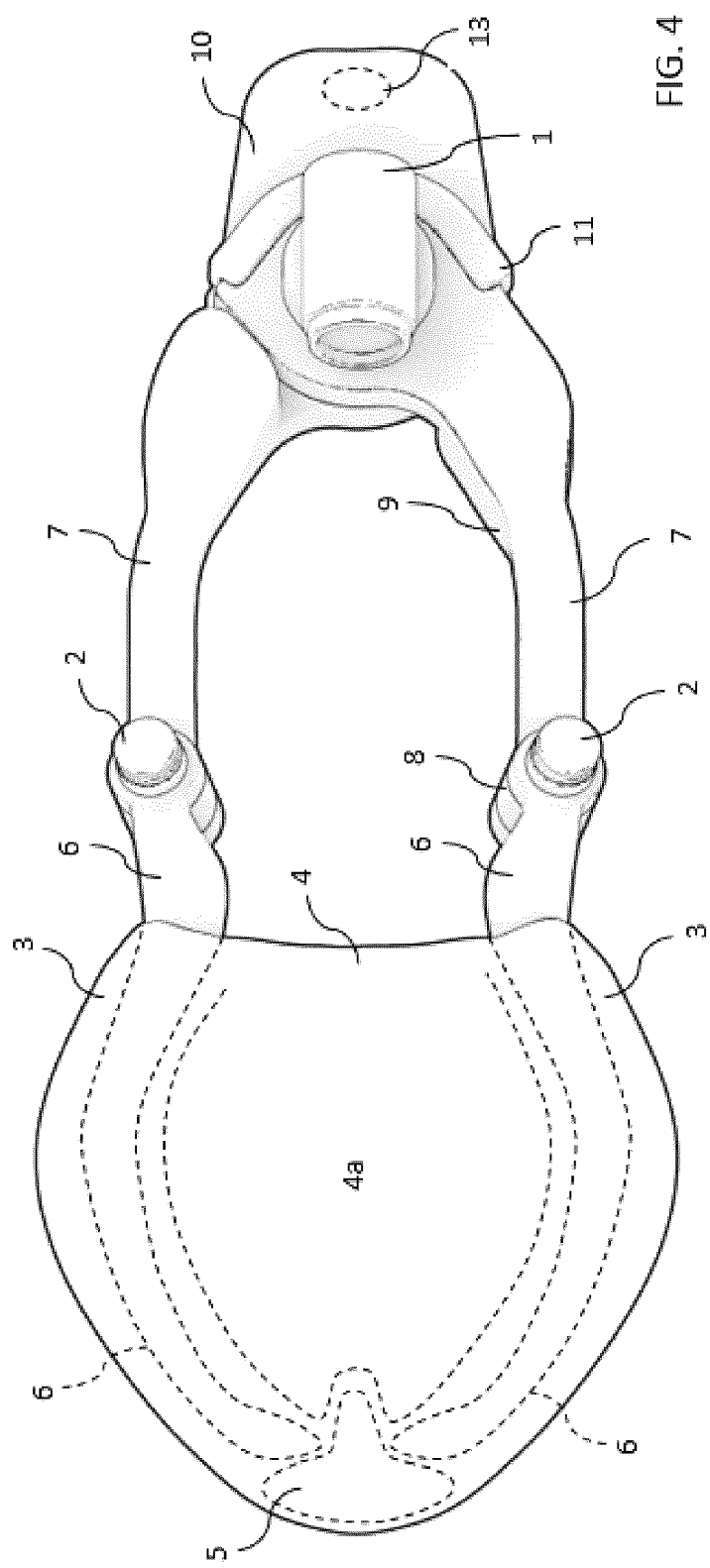
FIG. 4 is a top view of the device of FIG. 1.
Figure 5:
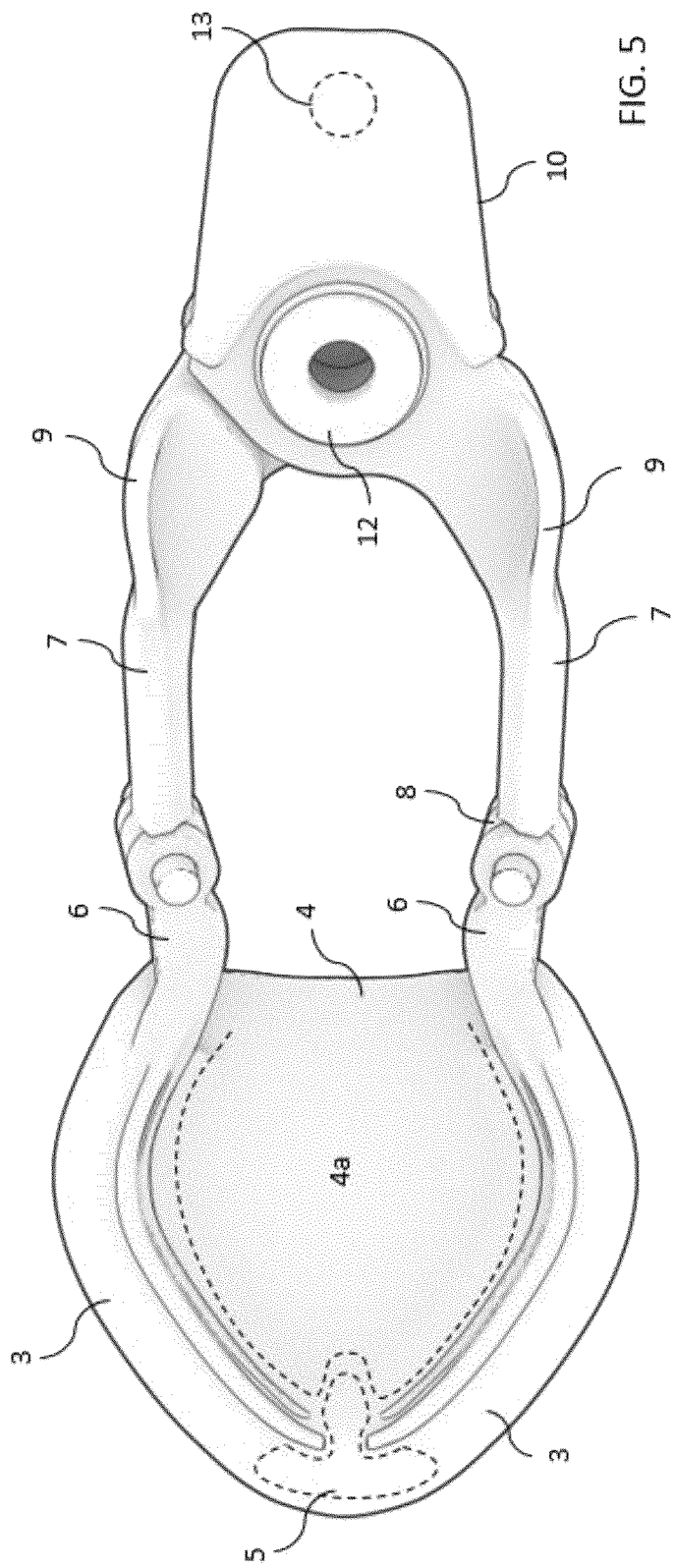
FIG. 5 is a bottom view of the device of FIG. 1.
Figure 6:
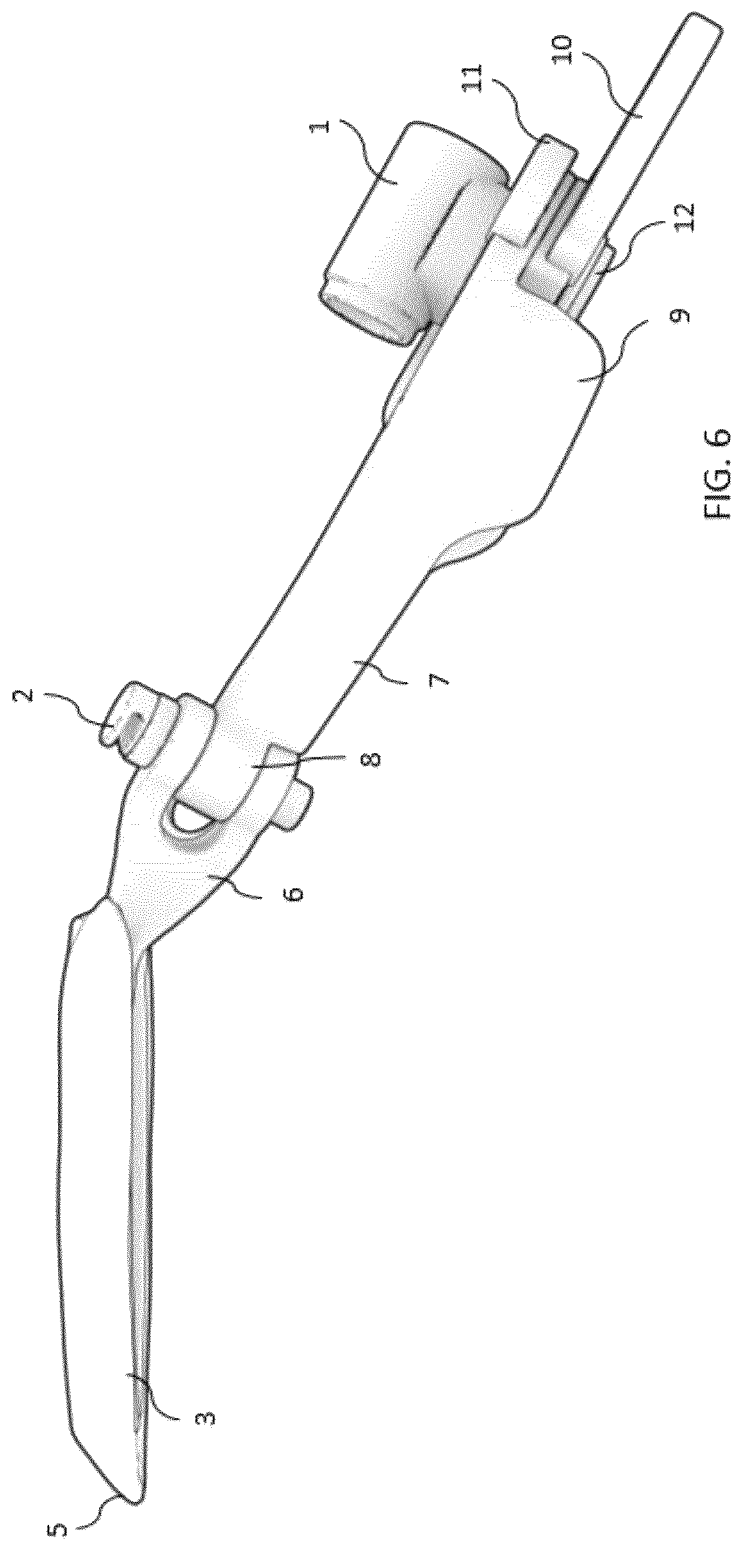
FIG. 6 is a side view of the device of FIG. 1.
Figure 7:
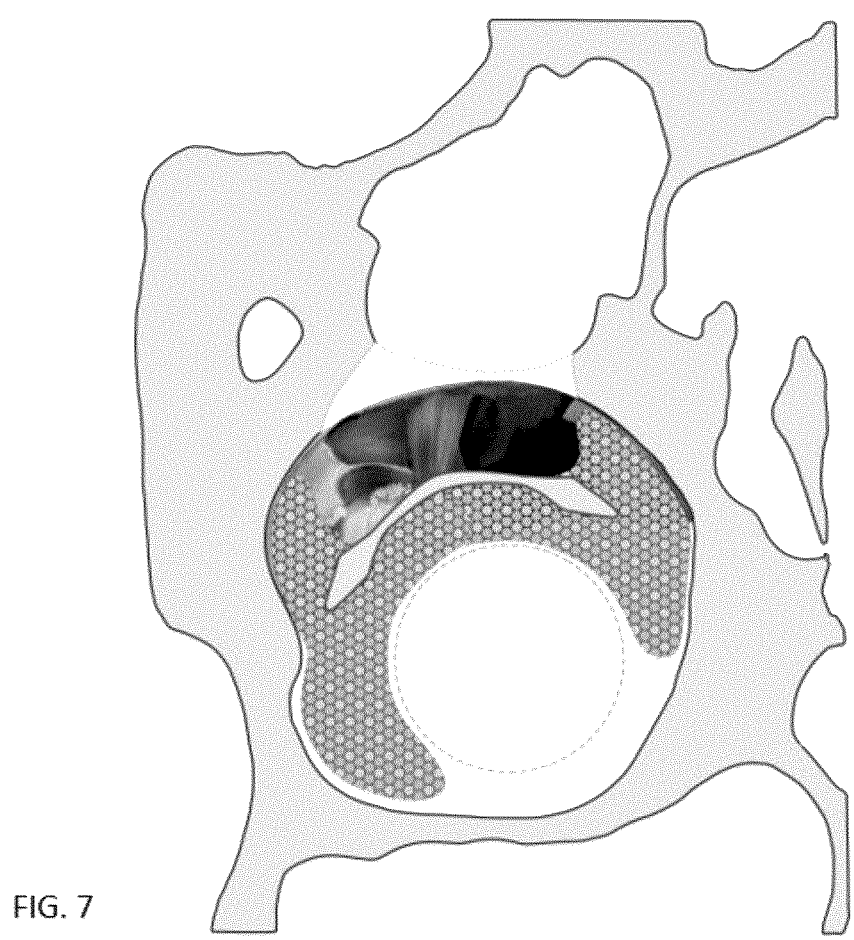
FIG. 7 is a schematic section of a patient's orbit showing a typical retractor in an initial contracted position, the problem of orbital fat obscuring defect and how the fat bypasses typical retractor designs that do not compensate for orbital shape.
Figure 8:
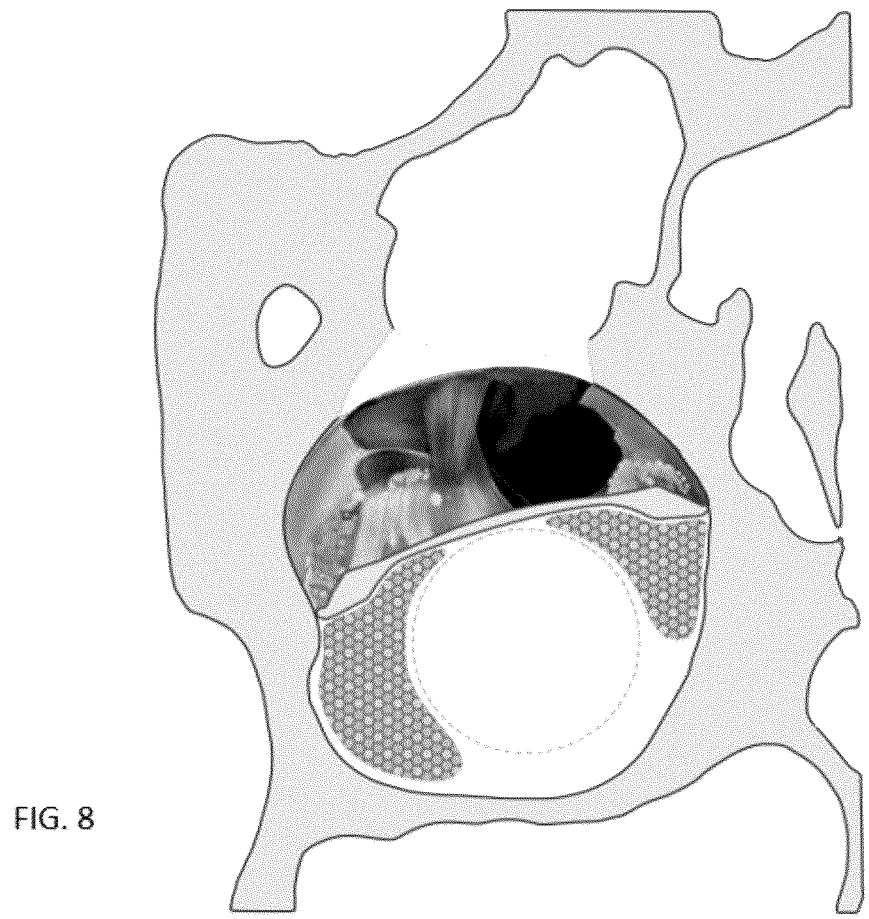
FIG. 8 is a schematic section (view from front) of a patient's orbit showing the DOAR in expanded position, overcoming the problem.

A further non-limiting embodiment of the handle/body and flexible head sections will be described and illustrated with respect to FIGS. 1 to 15. FIG. 1 shows orthographic view of an embodiment of the deep orbital access retractor (DOAR) showing primary components, FIG. 2 is a front view of the device of FIG. 1, FIG. 3 is a back view of the device of FIG. 1, FIG. 4 is a top view of the device of FIG. 1, FIG. 5 is a bottom view of the device of FIG. 1, and FIG. 6 is a side view of the device of FIG. 1. FIG. 7 is a schematic section of a patient's orbit showing a typical retractor in an initial contracted position, the problem of orbital fat obscuring defect and how the fat bypasses typical retractor designs that do not compensate for orbital shape, and FIG. 8 is a schematic section (view from front) of a patient's orbit showing the DOAR in expanded position, overcoming the problem.

Figure 9:
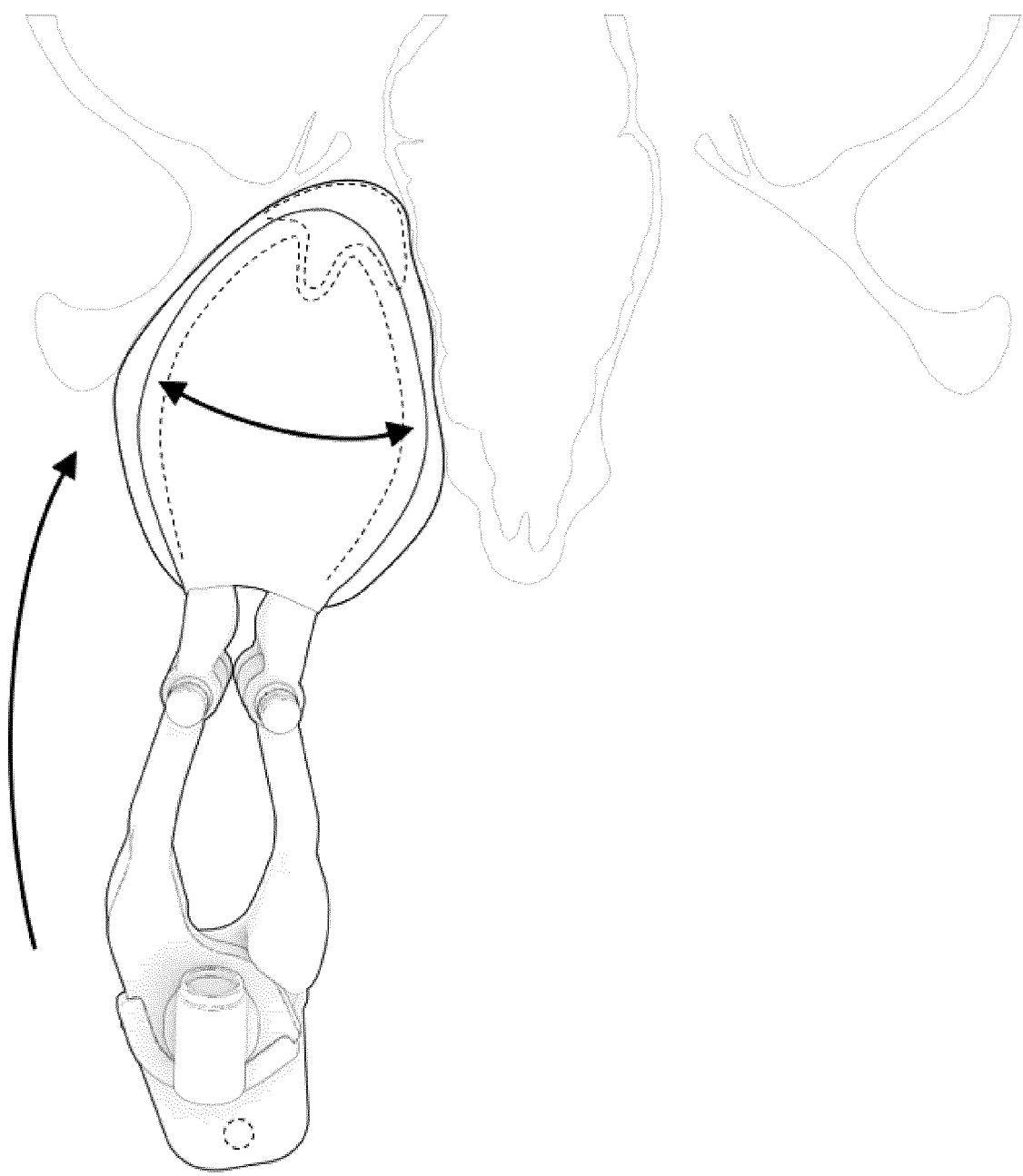
FIG. 9 is a schematic section (view from above) with the DOAR in orbit illustrating that the device can articulate in several directions for alignment, and as the retractor head expands, the flexible flange conforms to the irregular orbit shape with the head being capable of asymmetrical alignment.
Figure 10:
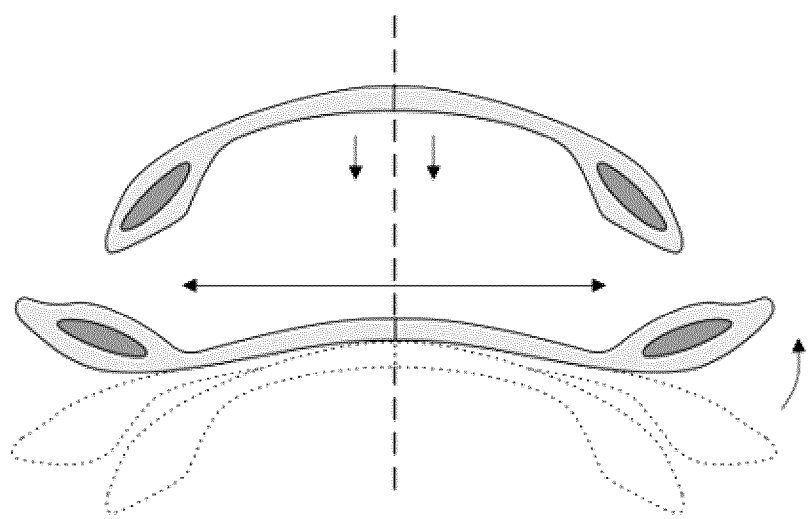
FIG. 10 is a schematic section (front view) showing the lateral expansion and flexion in the retractor head and the related flange deformation as it aligns with the orbital walls, with variable material properties to achieve desired rigidity or flexibility.

FIG. 9 is a schematic section (view from above) with the DOAR in orbit illustrating that the device can articulate in several directions for alignment, and as the retractor head expands, the flexible flange conforms to the irregular orbit shape with the head being capable of asymmetrical alignment, FIG. 10 is a schematic section (front view) showing the lateral expansion and flexion in the retractor head and the related flange deformation as it aligns with the orbital walls, with variable material properties to achieve desired rigidity or flexibility.

Figures 11, 12:
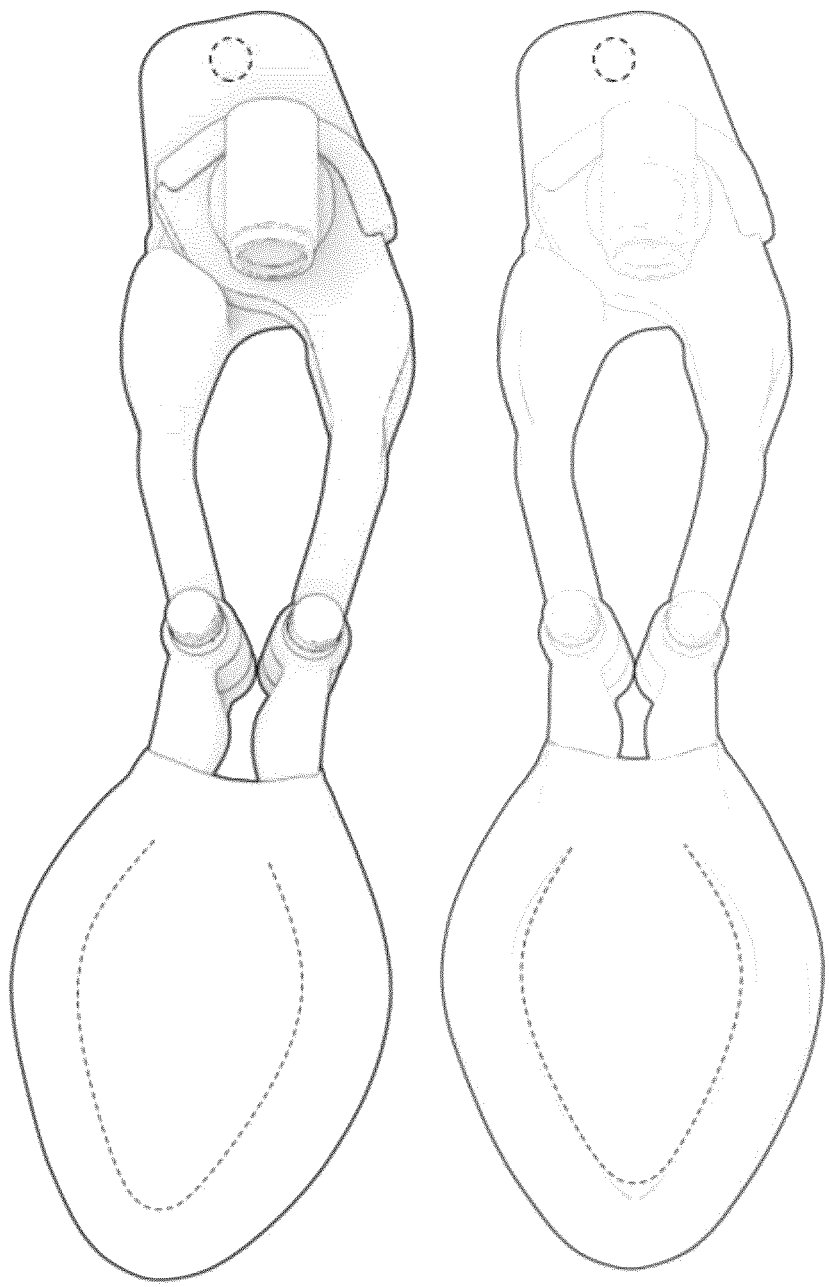
Figure 13:
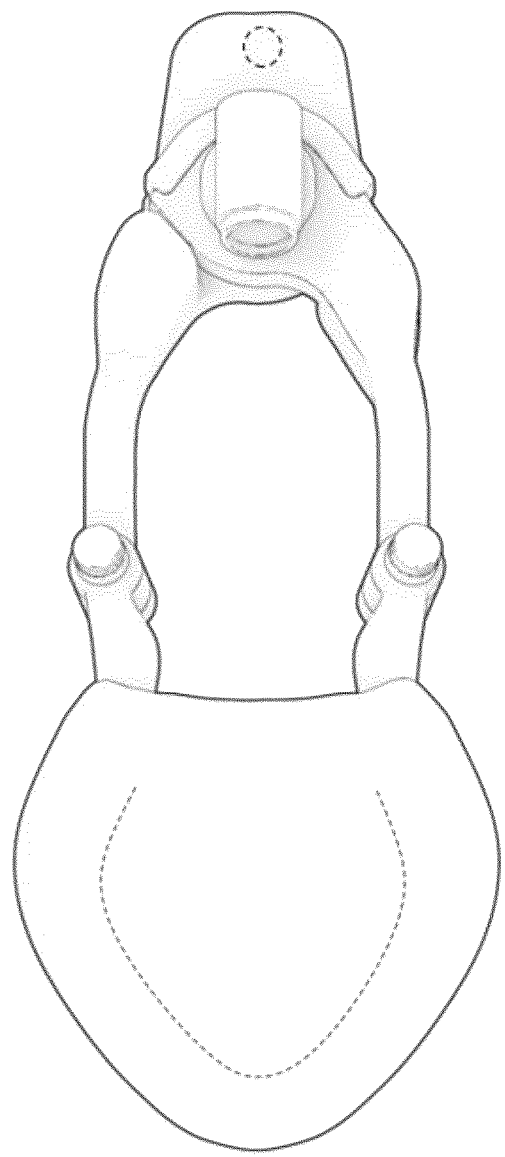
FIG. 13 shows the retractor with frame in open, straight position.

FIG. 11 shows the retractor with frame in closed, bent (right panel) position and the left panel is similar, FIG. 12 shows the retractor with frame in closed, straight position, and FIG. 13 shows the retractor with frame in open, straight position.

Figure 14:
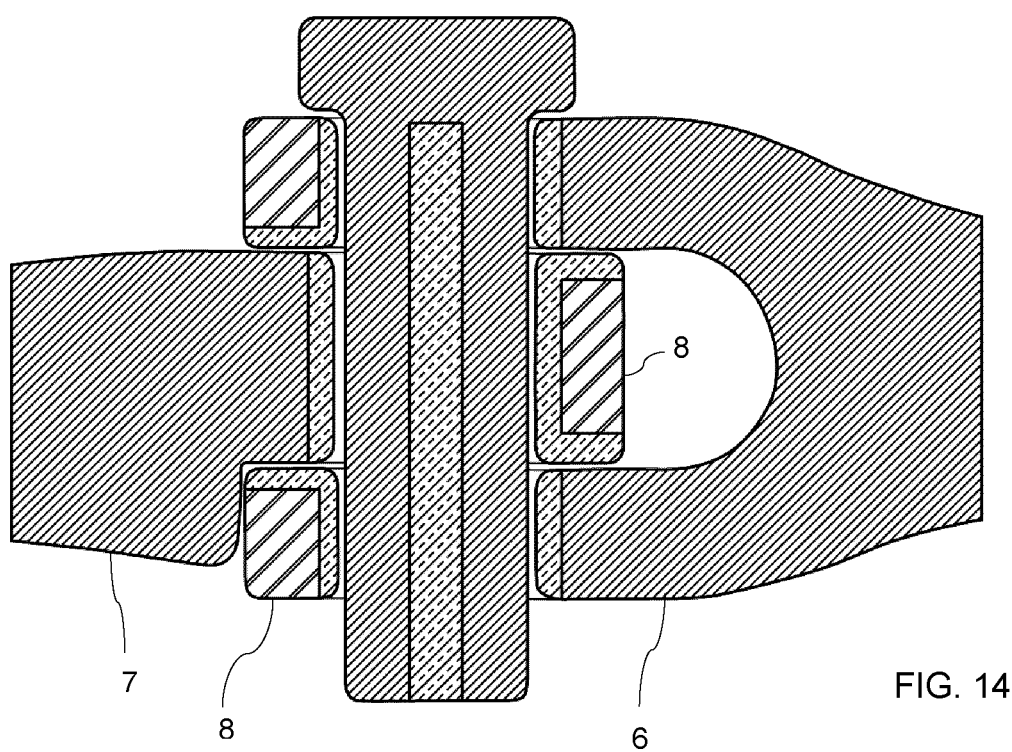
FIG. 14 shows a schematic joint section (trailing+power arm) showing possible arrangement of materials with varying density/flexibility.
Figure 15:
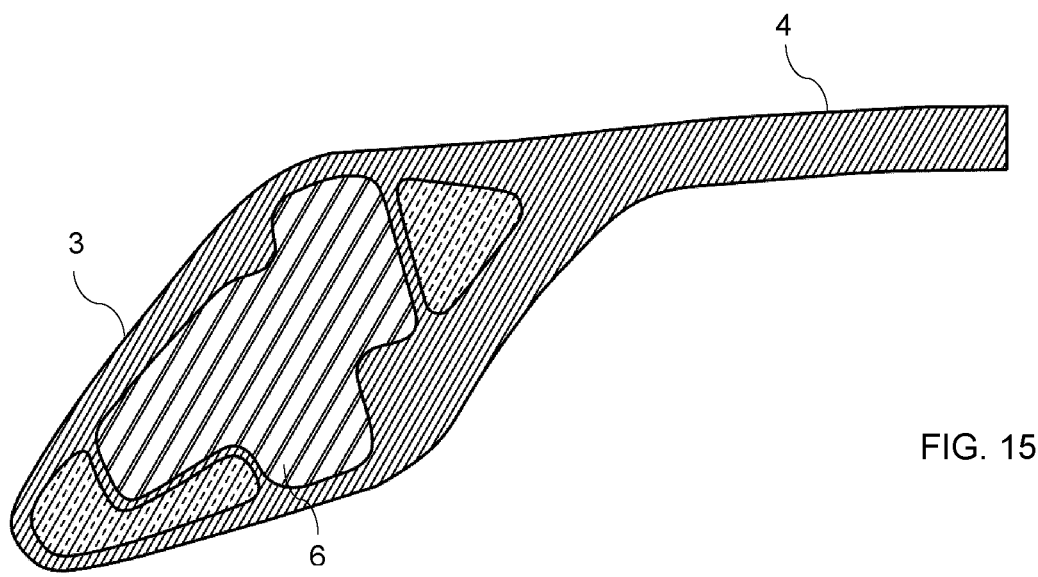
FIG. 15 shows a schematic partial section through head assembly showing possible arrangement of materials with varying density/flexibility.
Figure 16:
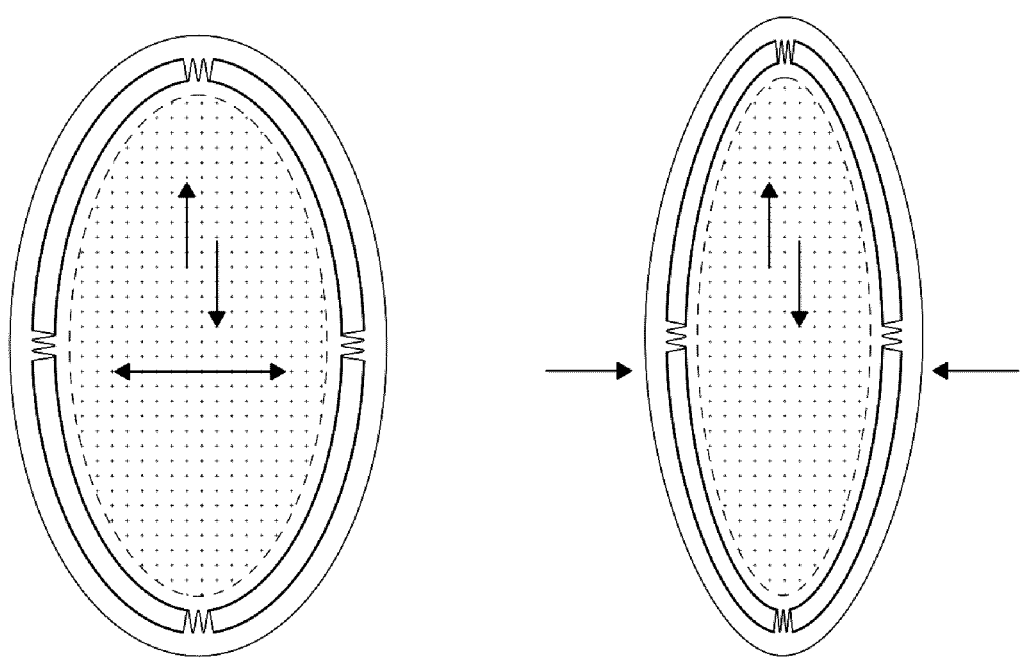
FIG. 16 shows a generic drawing of the self-expanding spoon-like orbital retractor.

FIG. 14 shows a schematic joint section (trailing+power arm) showing possible arrangement of materials with varying density/flexibility, while FIG. 15 shows a schematic partial section through flexible head assembly showing possible arrangement of materials with varying density/flexibility. FIG. 16 shows a generic drawing of the self-expanding spoon-like orbital retractor.

Referring to FIGS. 1 to 6, the deep orbital access retractor device is composed of a body section unit that provides mechanical force and support for a head section unit of the retractor, as shown in FIG. 1 in which the square brackets labelled body and head delineate these two sections. The body section is manipulated by the surgeon and acts as a fulcrum to make adjustments to the head section and allow for 6 DOF maneuvering within the orbit. The body section includes two geometrically opposed power arms (7) each having a proximal end and a distal end. The proximal ends are hinged together so that the two opposed power arms (7) can pivot with respect to each other. In an embodiment the hinge connection may include a flexible material located between the proximal ends so that they can flex with respect to each other instead pivoting in one plane as occurs in the absence of the flexible material. The distal ends include integrated hinge structures (8). The hinge structures (8) are hinged to the proximal ends of trailing arms (6). This hinge structure (8) may include a flexible material inserted between the respective ends of arms (7) and (6) to give out of plane flexibility as may be required. The arms (7) include finger pads (9) to facilitate manual control of the expansion and contraction of the device. The mechanical force is provided by a spring mechanism (12) such as a wire loop spring that is built into the power arms (6) of the body, with the loop section being located at the hinge point of the power arms (6) in handle (10) as shown. The spring mechanism could also be externally mounted, using a similar hinge point (12

Thus the present deep orbital device provides a self-expanding spoon shaped (or spoon-like) retractor that can be compressed to smaller size under single handed force applied by the clinician. The head section is comprised of a self-expanding rigid frame with a flexible perimeter that is able to conform to irregular contours.

More particularly, the DOAR frame as shown has as the spring mechanism (12) an integrated spring with a central loop with arms projecting at a preselected angle from the central loop (in the uncompressed state) where the central loop is wound around the central hinge connection between power arms (6) located in handle (10) and with the arms each embedded within a corresponding power arm (7). This spring mechanism (12) could also be mounted externally with the spring arms resting on the inner surfaces of the finger pads (9) or could exist as a flat spring that is opposed and runs from the central hinge point of each power arm (6) in handle (10) to the distal ends.

The body section may include (but is not essential) integrated light emitting diode (LED) lights (2) located at each trailing arm (6) hinge, that project forward into the orbital cavity. The power for each light is contained in the handle and arm assembly (10). These lights can be adjusted. Further, the body assembly contains a digital camera or sensor array (1) mounted at the hinge point of both power arms (7).

The electronics for the DOAR device are contained in the handle (10), and/or the power arms (7) and/or within a separate attachment that mounts to the handle (10) using the guide hole (13) and guide bar (11) as required. The guide bar (11) is mounted on handle (10) and provides a mechanical feature that enhances the stability of the mount. The guide hole (13) and guide bar (11) can also function as an alignment mount for image guided surgery targets and/or as a tie-off point for suture lines to immobilize the retractor or for delayed tying of sutures inserted in the field. The head assembly includes two geometrically opposed trailing arms (6) having proximal ends that connect to the distal ends of the power arms (7) and form the main functional component of the retractor. The trailing arms (6) each terminate at a distal end with a small gap between so that there are two separate arms (6).

Located in the gap between the distal ends of arms (6) is a flexible material (5) the purpose of which is to facilitate small amount of movement of the distal ends of arms (6) relative to each other so when in operation asymmetrical alignment of the distal ends of arms (6) can be attained to conform to the irregular geometry of the orbital walls. The trailing arms (6) may be made of the same material as arms (7) or could be made of a material of different density or rigidity.

The arms (6) are encapsulated with a flexible material of varying cross-section and varying density as required per region to achieve the desired expansion/contraction and flange (3) flexibility. This includes the tip and hinge (5), the elastic diaphragm or sling (4a), the proximal edge (4) and the flanges (3). The diaphragm (4a) and flange (3) could be integrally formed around the trailing arms (6) or they could be two separate structures with the thin flexible diaphragm (4a) bonded to the stiffer flange material (3). Alternatively, they can be made of the same material but the flange section (3) is thicker to make it more rigid. The diaphragm section (4a) is selected to have an elasticity such that it maintains tension across it regardless of compressing the arms (6) together thus bringing arms (7) together. Thus the elastic diaphragm section (4a) remains taught in both the expanded and contracted state of the device.

As shown in FIGS. 1, 4 and 5, the distal ends of the arc-shaped trailing arms (6) are spaced from each other by a small gap and the apex (5) of the head section in the vicinity of this gap is configured to provide a hinge-like structure to produce asymmetrical and/or universal movement and out-of-plane movement of these distal ends with respect to each other. Thus this hinge-like structure provides motion that is not a rigid pin connection that only allows rotation in one axis.

The distal ends of trailing arms (6) and the hinge-like structure are configured in such a way as to reduce the rigidity of a single hinge point at the apex or tip (5) and to impart a bending action in more than one plane. In one instance this can be achieved by creating a flexible gap between the distal ends of arms (6) that is then laminated into the flange and diaphragm assembly. In another instance the entire hinge point (5) could be a flexible material that is bonded and/or mechanically joined to the distal ends of arms, for example ball and socket (6). These are only two possible configurations and as those skilled in the art will appreciate there are numerous other ways to accomplish this functionality.

This hinge-like structure of apex (5) provides asymmetrical and/or universal movement and out-of-plane movement in the traditional hinge assembly. It is still rigid enough to provide the mechanical action required for the retractor motion without collapsing or flexing too far. This is controlled with the distal end geometry, the shape of the end connections and the material density variation.

The flexible diaphragm (4a) is connected to, and enveloped by, the flexible flange (3) as noted earlier. The opposed trailing arms (6) are coupled to a spring mechanism configured to bias the opposed arms away from each other. When a clinician squeezes the opposed arms (7) together the distal ends of the opposed arms (7) and the proximal ends of trailing arms (6) come together thereby causing the head section to narrow while undergoing minimal change of shape while the diaphragm (4a) stays substantially flat due to the maintained tension (analogous to a stretched balloon). The head section comprised of arms (6), flange (3), tip (5) and diaphragm (4) are configured to provide sufficient rigidity to "scoop" and apply significant force to the orbital contents, similar in function to a how a solid metal spoon would work but with the added feature of being expandable and compressible. The head can be manufactured in varying diameters to accommodate different sized orbits, as for example in paediatric cases and adults.

In operation, the deep orbital access retractor 10 works as follows. The power arms (7) are compressed by the Operator/Clinician squeezing the finger pads (9) together thus reducing the width of the head section while, due to its inherent elasticity, tension is maintained across the diaphragm (4a) so that it does not buckle and impede visualization during insertion of the retractor. The orbital contents are swept away from the operative site using conventional instrumentation, exposing the bone of one wall. The retractor is simultaneously inserted and compressed against that wall, while the finger pads (9) remain compressed together by the Operator.

With one side of the DOAR firmly compressed against one wall all the way to the deep apex of the field, the remaining orbital contents are swept out of the field as the Operator releases the compression on the DOAR finger pads (9), allowing expansion of the head section with the orbital contents barriered or trapped behind it.

The rate at which the Operator releases the compression on the spring mechanism will vary to allow for careful incremental repositioning of the orbital contents behind the retracting head thus ensuring complete retraction. The flexible flange (3) and the Operator's fine control of the release, minimizes the risk of trapping orbital contents between the DOAR and the boney walls and due to the flexibility of the flange, ensures that if orbital contents are mistakenly trapped between the retractor and bone there will be no crush injury (as is the case with a rigid retractor). Movement of the trailing arms (6) also allows for quick release of any mistakenly trapped tissues without the loss of compression barrier in other parts of the field.

The design and configuration of the present deep orbital access retractor provides the Operator very fine continuous control over the expansion of the flexible diaphragm (4a) and it has the ability to expand differential or asymmetrically so that the Operator can maintain the barrier on one side while releasing potentially trapped contents on the other side with fine finger compression, sweeping that up and then releasing the device to expand to that side.

The deep orbital access retractor device disclosed herein is very advantageous in that the flexible perimeter flange (3) allows device to conform to the variable anatomy of any boney cavity and therefore facilitates the formation of a sealed barrier between the tissues being retracted and the cavity to be accesses and or visualized. The progressive expansile nature of retractor allows for progressive seal (as just noted) from the distal tip (5) of the retractor (deepest point) to the proximal part (4) of the retractor head allowing for progressive repositioning of tissue to be retracted, behind the retractor head making retraction more effective and efficient. The device expands from tip (5) to the back (4) allowing surgeon to move tissue behind retractor head as it expands making "entrapment" of tissue between retractor perimeter and bone less likely.

The rotation of flange (3) upward (as depicted in FIG. 10) allows for retracted soft tissue to be swept "up" behind retractor head and out of operative field thereby once again making "entrapment" of tissue between retractor perimeter and bone less likely.

In addition, the diaphragm (4a) allows maintenance of consistent pressure of the flexible barrier to retracted contents which this is less likely to cause damage to vital organs such as the globe for instance.

As the entire structure of the retractor head (FIG. 1) is made of a combination of rigid and flexible materials, including the pivot point at the integrated tip, the expansion can be asymmetrical in response to the resistance of the bone it encounters in its expansion as shown in FIG. 9. The arms must be rigid enough to generate the leverage required to retract deeply.

The present deep orbital access retractor very advantageously provides a head assembly which is configured to allow for asymmetrical movement by way of a tip (5) design that functions as a flexible hinge, with a composite arrangement of materials that enhance both rigid and flexible behavior in the head section. This allows the retractor to expand and contract for placement, sweep soft tissue out of the field of view and to conform accurately to the existing bone.

The present orbital retractor is very advantageous in that it only requires one hand (two digits) of the clinician to operate the device while leaving the other hand free, unlike current expanding devices which require two handed operation.

Figure 17:
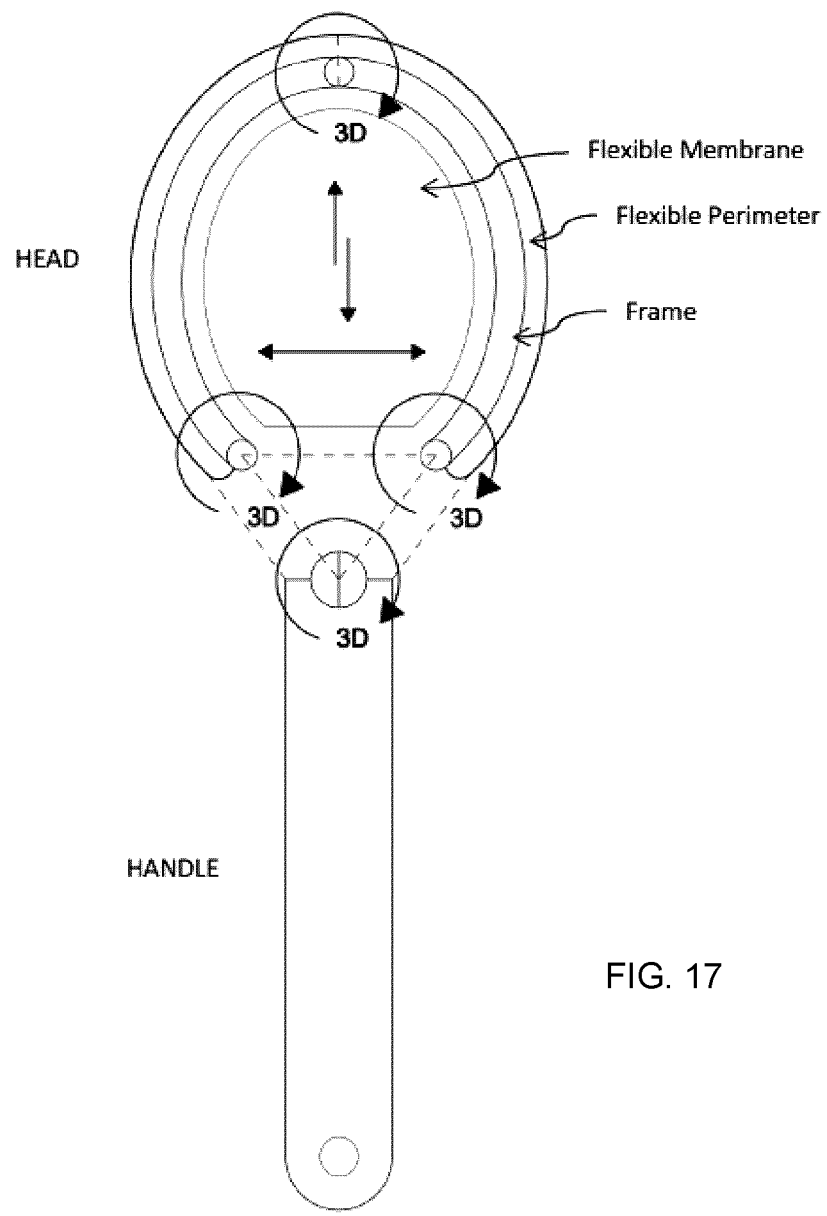
FIG. 17 shows a generic figure of the present DOAR device which includes a self-expanding "spoon" shaped retractor (or spoon-like) which comprising a flexible head section and handle.

FIG. 17 shows a generic figure of the DOAR device which includes a self-expanding "spoon" shaped retractor (or spoon-like) which comprising a flexible head section and handle. The head section comprises a self-expanding rigid frame with a flexible perimeter that is able to conform to irregular contours and includes an elastic diaphragm that remains taught in both the expanded and contracted state of the device. The head frame includes universal articulations that enable out-of-plane movement and asymmetrical movements that facilitate the device conforming to asymmetric and irregular anatomic contours. The DOAR device allows for dynamic movement that is automatic, simultaneous, multi-planar movement and facilitates the retraction of soft tissues and the conforming of the seal of the device and allows for automatic folding up and reduction of cross section prior to insertion.

In summary, a non-limiting embodiment of a deep orbital access retractor, comprises a compressible handle section having a size and shape to be manipulated by at least two (2) digits of a clinician; a flexible head section having two (2) arms with each arm having a distal end and a proximal end, the distal ends of the arms spaced apart forming a gap there-between at a distal tip section, a flexible flange material enveloping and enclosing the two arms and the gap and extending around a periphery of the flexible head section, and including a flexible diaphragm attached to and extending between the to arms to provide a generally spoon-shaped flexible head section. The flexible head section is linked to the compressible handle section with the linkage between the compressible handle section and the proximal ends of the trailing arms being configured such that upon compression of the handle section the arms articulate with respect to each other thereby causing narrowing of the flexible head section to allow for insertion into the orbit and positioning between soft tissue and bone while the flexible diaphragm remains in sufficient tension to not obstruct the view of the operator into the orbit. When compression is released the flexible diaphragm develops sufficient tension and rigidity for applying sufficient force to retract the orbital contents of a patient to allow access to orbital walls.

In an embodiment the flexible flange material enveloping and enclosing the two arms and the gap has a material density variation in a vicinity of the gap configured to produce a hinge-like structure of the distal tip section that provides asymmetrical or universal movement and out-of-plane movement of the distal ends of arms.

In an embodiment the deep orbital access retractor includes a deformable material located in the gap between the distal ends of the arms and abutting against the distal ends of the arms.

In an embodiment there is provided a deep orbital access retractor, comprising:
 a) a compressible handle section having a size and shape to be manipulated by at least two (2) digits of a clinician;
 b) a flexible head section having two geometrically opposed and arc-shaped arms each having a proximal end and a distal end, the distal ends of the arc-shaped arms being spaced from each other by a gap at a distal tip section, each trailing arc-shaped arm being linked at its proximal end to the compressible handle section, a flexible flange material attached to the arc-shaped arms and extending around a periphery of the flexible head section and enclosing the gap at the distal tip section, a flexible diaphragm attached to and extending between the arc-shaped arms, the distal ends of the arc-shaped arms having a geometry and shape and the flange material enveloping the distal tip section having a material density variation configured to produce a hinge-like structure of the distal tip section that provides asymmetrical or universal movement and out-of-plane movement of the distal ends of arc-shaped arms; and
the linkage between the compressible handle section and the proximal ends of the arc-shaped arms being configured such that upon compression of the handle section the arms articulate with respect to each other thereby causing narrowing of the flexible head section to allow for insertion into the orbit and positioning between soft tissue and bone while the flexible diaphragm remains in sufficient tension to not obstruct the view of the operator into the orbit, and wherein when compression is released the diaphragm develops sufficient tension and rigidity for applying sufficient force to retract the orbital contents of a patient to allow access to the orbital walls.

In an embodiment the flange material enveloping and enclosing the two arc-shaped arms and the gap has a material density variation in a vicinity of the gap configured to produce a hinge-like structure of the distal tip section that provides asymmetrical or universal movement and out-of-plane movement of the distal ends of the arc-shaped arms.

In an embodiment the deep orbital access retractor includes a deformable material located in the gap between the distal ends of the arc-shaped arms and abutting against the distal ends of the arc-shaped arms.

In an embodiment a deep orbital access retractor is provides, comprising:
a) a manipulable body section including a handle and two geometrically opposed handle arms each having a distal end and a proximal end, the proximal ends being hinged on the handle; and
b) a flexible head section having two geometrically opposed and arc-shaped trailing arms each having a proximal end and a distal end with each trailing arm being hinge connected at its proximal end to a corresponding distal end of one of the opposed handle arms, the distal ends of the arc-shaped trailing arms being spaced from each other by a gap at a distal tip section, each of the arc-shaped trailing arms and the gap being enveloped by a flexible flange material extending around a periphery of the flexible head section, a flexible diaphragm being connected to the trailing arms to form a generally spoon shaped flexible head section, the distal ends having a geometry and shape and the flange material enveloping the distal tip section having a material density variation configured to produce a hinge-like structure of the distal tip section that provides asymmetrical or universal movement and out-of-plane movement of the distal ends of trailing arms; and
the opposed handle arms coupled to a biasing mechanism configured to bias the opposed handle arms away from each other, and whereupon when a clinician squeezes the opposed handle arms together the distal ends of the opposed handle arms and the proximal ends of the arc-shaped trailing arms come together thereby causing narrowing of the flexible head section to allow for insertion into the orbit and positioning between soft tissue and bone while the flexible diaphragm remains in sufficient tension to not obstruct the view of the operator into the orbit, and wherein when compression is released the diaphragm develops sufficient tension and rigidity for applying sufficient force to the orbital contents of a patient to allow access to the orbital walls.

In an embodiment the deep orbital access retractor device includes a flexible material separating the distal ends of the opposed handle arms and the proximal ends of the arc-shaped trailing arms in each hinge connection to provide an extra degree of freedom of movement of the opposed handle arms and the proximal ends of the arc-shaped trailing arms.

In an embodiment the deep orbital access retractor device further includes a flexible material separating the proximal ends of the opposed handle arms in the hinge connection in the handle to provide an extra degree of freedom of movement of the opposed handle arms and the proximal ends of the arc-shaped trailing arms.

In an embodiment the deep orbital access retractor device further includes a flexible material located in the gap separating the distal ends of the arc-shaped trailing arms to provide an extra degree of freedom of movement of the distal ends of the arc-shaped trailing arms.

In an embodiment the deep orbital access retractor device further includes a camera mounted on the handle having a field of view including the flexible head section.

In an embodiment the deep orbital access retractor device further includes at least one light source mounted thereon to illuminate a surgical area of a patient that the device is being used on.

In an embodiment the deep orbital access retractor device further includes a light source mounted on each hinge connection of the arc-shaped trailing arms to the geometrically opposed handle arms.

In an embodiment each light source is a light emitting diode.

In an embodiment the deep orbital access retractor further includes a power supply located in the handle electrically connected to the camera and the light source.

In an embodiment the biasing mechanism is a spring mechanism is built into the geometrically opposed handle arms configured to bias them apart.

In an embodiment the deep orbital access retractor device further comprises finger pads mounted adjacent to the proximal ends of the geometrically opposed handle arms and having size and shape to accommodate the digits of a clinician.

In an embodiment the flexible diaphragm and the flexible flange are a single unitary piece made of the same material with the flexible flange being thicker than the flexible diaphragm so that it is more rigid than the flexible diaphragm.

In an embodiment the flexible diaphragm and the flexible flange are made of separate materials with the flexible flange being made of a material that is more rigid than the flexible diaphragm, and wherein the flexible diaphragm is bonded to the flexible flange.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A deep orbital access retractor, comprising:
a) a compressible handle section having a size and shape to be manipulated by at least two digits of a clinician;
b) a flexible head section having two geometrically opposed and arc-shaped trailing arms with each arc-shaped trailing arm of the arc-shaped trailing arms having a distal end, a proximal end, and being arc-shaped along an entire length of the arc-shaped trailing arm, said distal ends of said arc-shaped trailing arms spaced apart forming a gap there-between at a distal tip section, a flexible flange material enveloping and enclosing said two arc-shaped trailing arms and said gap and extending around a periphery of said flexible head section, and including a flexible diaphragm attached to and extending between said arc-shaped trailing arms to provide an expandable and collapsible generally spoon-shaped flexible head section; and
c) said flexible head section being linked to said compressible handle section with a linkage between said compressible handle section and said proximal ends of said trailing arms being configured such that a longitudinal axis of the flexible head section is different than a longitudinal axis of the compressible handle section and upon compression of said handle section said arc-shaped trailing arms articulate with respect to each other thereby causing narrowing of the flexible head section to allow for insertion into the orbit and positioning between soft tissue and bone while said flexible diaphragm remains in sufficient tension to not obstruct the view of the operator into the orbit, and wherein when compression is released the flexible diaphragm develops sufficient tension and rigidity for applying sufficient force to retract the orbital contents of a patient to allow access to orbital anatomy.

2. The deep orbital access retractor according to claim 1, wherein said flange material enveloping and enclosing said two arms and said gap has a material density variation in a vicinity of said gap configured to produce a hinge-like structure of said distal tip section that provides asymmetrical or universal movement and out-of-plane movement of said distal ends of said arc-shaped trailing arms that facilitate the flexible head section conforming to asymmetric and irregular anatomic contours.

3. The deep orbital access retractor according to claim 1, including a deformable material located in said gap between said distal ends of said arc-shaped trailing arms and abutting against said distal ends of said arc-shaped trailing arms.

4. A deep orbital access retractor, comprising:
a) a compressible handle section having a size and shape to be manipulated by at least two digits of a clinician;
b) a flexible head section having two geometrically opposed and arc-shaped trailing arms, each arc-shaped trailing arm of the arc-shaped trailing arms having a proximal end, a distal end, and being arc-shaped along an entire length of the arc-shaped trailing arm, said distal ends of said arc-shaped trailing arms being spaced from each other by a gap at a distal tip section, each trailing arc-shaped trailing arm being linked at its proximal end to said compressible handle section, a flexible flange material attached to said arc-shaped trailing arms and extending around a periphery of said flexible head section and enclosing said gap at said distal tip section, a flexible diaphragm attached to and extending between said arc-shaped trailing arms to provide an expandable and collapsible generally spoon-shaped flexible head section, said distal ends of said arc-shaped trailing arms having a geometry and shape and said flange material enveloping said distal tip section having a material density variation configured to produce a hinge-like structure of said distal tip section that provides asymmetrical or universal movement and out-of-plane movement of said distal ends of arc-shaped trailing arms that facilitate the flexible head section conforming to asymmetric and irregular anatomic contours; and
a linkage between said compressible handle section and said proximal ends of said arc-shaped trailing arms configured so that a longitudinal axis of the flexible head section is different than a longitudinal axis of the compressible handle section and being configured such that upon compression of said handle section said arc-shaped trailing arms articulate with respect to each other thereby causing narrowing of the flexible head section to allow for insertion into the orbit and positioning between soft tissue and bone while said flexible diaphragm remains in sufficient tension to not obstruct the view of the operator into the orbit, and wherein when compression is released the diaphragm develops sufficient tension and rigidity for applying sufficient force to retract the orbital contents of a patient to allow access to the orbital anatomy.

5. The deep orbital access retractor according to claim 4, wherein said flange material enveloping and enclosing said two arc-shaped trailing arms and said gap has said material density variation in a vicinity of said gap configured to produce said hinge-like structure of said distal tip section that provides said asymmetrical or universal movement and out-of-plane movement of said distal ends of said arc-shaped trailing arms.

6. The deep orbital access retractor according to claim 4, including a deformable material located in said gap between said distal ends of said arc-shaped trailing arms and abutting against said distal ends of said arc-shaped trailing arms.

7. A deep orbital access retractor, comprising:
a) a manipulable body section including a handle and two geometrically opposed handle arms each having a distal end and a proximal end, said proximal ends being hinged on the handle; and
b) a flexible head section having two geometrically opposed and arc-shaped trailing arms, each arc-shaped trailing arm having a proximal end, a distal end, and being arc-shaped along an entire length of the arc-shaped trailing arm, with each said arc-shaped trailing arm being connected at its proximal end to a corresponding distal end of one of said opposed handle arms through a linkage configured so that a longitudinal axis of the flexible head section is different than a longitudinal axis of the handle arms, said distal ends of said arc-shaped trailing arms being spaced from each other by a gap at a distal tip section, each of said arc-shaped trailing arms and said gap being enveloped by a flexible flange material extending around a periphery of said flexible head section, a flexible diaphragm being connected to said arc-shaped trailing arms to form an expandable and collapsible generally spoon shaped flexible head section, said distal ends having a geometry and shape and said flange material enveloping said distal tip section having a material density variation configured to produce a hinge-like structure of said distal tip section that provides asymmetrical or universal movement and out-of-plane movement of said distal ends of said arc-shaped trailing arms that facilitate the flexible head section conforming to asymmetric and irregular anatomic contours; and
c) said opposed handle arms coupled to a biasing mechanism configured to bias said opposed handle arms away from each other, and whereupon when a clinician squeezes said opposed handle arms together said distal ends of said opposed handle arms and said proximal ends of said arc-shaped trailing arms come together thereby causing narrowing of the flexible head section to allow for insertion into the orbit and positioning between soft tissue and bone while said flexible diaphragm remains in sufficient tension to not obstruct the view of the operator into the orbit, and wherein when compression is released the diaphragm develops sufficient tension and rigidity for applying sufficient force to the orbital contents of a patient to allow access to the orbital anatomy.

8. The deep orbital access retractor according to claim 7, including a first flexible material separating said distal ends of said opposed handle arms and said proximal ends of said arc-shaped trailing arms in each hinge connection to provide an extra degree of freedom of movement of said opposed handle arms and said proximal ends of said arc-shaped trailing arms.

9. The deep orbital access retractor according to claim 8, including a second flexible material separating said proximal ends of said opposed handle arms in said hinge connection in said handle to provide an extra degree of freedom of movement of said opposed handle arms and said proximal ends of said arc-shaped trailing arms.

10. The deep orbital access retractor according to claim 9, including a third flexible material located in said gap separating said distal ends of said arc-shaped trailing arms to provide an extra degree of freedom of movement of said distal ends of said arc-shaped trailing arms.

11. The deep orbital access retractor according to claim 7, further comprising a camera mounted on said handle having a field of view including said flexible head section.

12. The deep orbital access retractor according to claim 7, including at least one light source mounted thereon to illuminate a surgical area of a patient that the deep orbital access retractor is being used on.

13. The deep orbital access retractor according to claim 7, including a light source mounted on each hinge connection of said arc-shaped trailing arms to said geometrically opposed handle arms.

14. The deep orbital access retractor according to claim 12, wherein each light source is a light emitting diode.

15. The deep orbital access retractor according to claim 11, including a power supply located in said handle electrically connected to said camera and a light source mounted on the deep orbital access retractor having a field of view including said flexible head section.

16. The deep orbital access retractor according to claim 7, wherein said biasing mechanism is a spring mechanism is built into the geometrically opposed handle arms configured to bias them apart.

17. The deep orbital access retractor according to claim 7, further comprising finger pads mounted adjacent to the proximal ends of said geometrically opposed handle arms and having size and shape to accommodate the digits of a clinician.

18. The deep orbital access retractor according to claim 7, wherein said flexible diaphragm and said flexible flange are a single unitary piece made of the same material with said flexible flange being thicker than said flexible diaphragm so that it is more rigid than said flexible diaphragm.

19. The deep orbital access retractor according to claim 7, wherein said flexible diaphragm and said flexible flange are made of separate materials with said flexible flange being made of a material that is more rigid than said flexible diaphragm, and wherein said flexible diaphragm is bonded to said flexible flange.

* * * * *